United States Patent
Reimer et al.

(10) Patent No.: US 10,168,200 B2
(45) Date of Patent: Jan. 1, 2019

(54) SYSTEMS AND METHODS FOR POWER MANAGEMENT IN ULTRASONIC SENSORS

(71) Applicant: SSI Technologies, Inc., Janesville, WI (US)

(72) Inventors: Lawrence B. Reimer, Georgetown, SC (US); Gregory P. Murphy, Janesville, WI (US)

(73) Assignee: SSI Technologies, Inc., Janesville, WI (US)

( * ) Notice: Subject to any disclaimer, the term of this patent is extended or adjusted under 35 U.S.C. 154(b) by 188 days.

(21) Appl. No.: 15/233,476

(22) Filed: Aug. 10, 2016

(65) Prior Publication Data
US 2018/0045554 A1 Feb. 15, 2018

(51) Int. Cl.
*G01F 25/00* (2006.01)
*G01F 23/296* (2006.01)
*G01N 29/024* (2006.01)
*G01N 29/34* (2006.01)

(52) U.S. Cl.
CPC ........ *G01F 25/0061* (2013.01); *G01F 23/296* (2013.01); *G01F 23/2962* (2013.01); *G01N 29/024* (2013.01); *G01N 29/34* (2013.01); *G01N 2291/022* (2013.01); *G01N 2291/02818* (2013.01); *G01N 2291/02836* (2013.01); *G01N 2291/101* (2013.01)

(58) Field of Classification Search
CPC .... G01F 23/28; G01F 23/296; G01F 23/2962; G01F 23/2968; G01F 25/0061; G01H 3/10; G01H 11/06; G01H 11/08; G01N 29/02; G01N 29/22; G01N 29/2437; G01N 29/32; G01N 29/346; G01N 29/40; G01N 29/4409; G01N 29/4454; G01N 29/4463; G01N 29/48
USPC .......... 73/1.73, 1.82, 1.83, 32 A, 64.53, 596, 73/632, 641, 645, 646, 861.18
See application file for complete search history.

(56) References Cited

U.S. PATENT DOCUMENTS

| 5,831,168 A * | 11/1998 | Shinomura ........ G01N 29/0609 600/437 |
| 6,573,732 B1 | 6/2003 | Reimer |
| 8,733,153 B2 | 5/2014 | Reimer et al. |
| 2007/0203668 A1 | 8/2007 | Reimer et al. |
| 2012/0118059 A1 | 5/2012 | Reimer et al. |

OTHER PUBLICATIONS

International Search Report and Written Opinion for Application No. PCT/US2017/046080 dated Oct. 12, 2017 (13 pages).

* cited by examiner

*Primary Examiner* — Benjamin Schmitt
(74) *Attorney, Agent, or Firm* — Michael Best & Friedrich LLP

(57) ABSTRACT

A system and method for controlling the energy of sound waves generated for fluid sensing. The system includes a transducer configured to generate a first sound wave and a second sound wave and to detect a first echo of the first and second sound waves. The system also includes a driver configured to drive the transducer to produce the first and second sound waves. The system also includes a controller configured to compare a signal characteristic of the first echo of the first and second sound waves. The controller is configured to control the driver based on comparing the signal characteristic of the first echo of the first and second sound waves.

15 Claims, 4 Drawing Sheets

SYSTEMS AND METHODS FOR POWER MANAGEMENT IN ULTRASONIC SENSORS

BACKGROUND

Ultrasonic transducers can be used for measuring the level of a fluid (for example, diesel exhaust fluid (DEF)) in a container as well as a specific gravity of the fluid to determine the quality, concentration, viscosity or grade (in the case of oils) of the fluid. The transducer is positioned at either the top or bottom of a tank containing the fluid. An ultrasonic signal is generated by the transducer and the time it takes for the signal to travel from the transducer at the top or bottom of a tank to the surface of the fluid, reflect off the surface of the fluid, and return to the transducer is measured. Phase errors and lobe shift errors may be introduced while measuring the ultrasonic signal reflected off the surface of the fluid as a result of sloshing of the fluid, thermocline within the fluid, and other reasons. These errors affect accurate measurement of the various characteristics of the fluid.

SUMMARY

One aspect of the invention provides an algorithm to manage measurement errors in a fluid sensing system by controlling the energy of the sound wave such that the received echo amplitude is maintained at a as constant of level as possible from one to the next. Phase errors, amplitude differences and lobe shifts from one echo return to the next are all indications of changing amplitude in the received echo. By measuring one or all of these characteristics one can increase or decrease the sound energy as may be required to reduce time measurement error effect associated with return echo amplitude and thereby increase the accuracy and repeatability of the time measurement.

One exemplary embodiment provides a system for controlling the energy of sound waves generated in a fluid sensing system. The fluid sensing system includes a transducer, a controller and a driver. The transducer is configured to generate a first sound wave and a second sound wave in a tank having a fluid and to detect a first echo of the first and second sound waves. The controller is configured to compare a signal characteristic of the first echo of the first and second sound waves. The driver is configured to drive the transducer based on comparing the signal characteristic of the first echo of the first and sound waves.

Another exemplary embodiment provides a method of controlling a lobe shift, wherein the timing differences between adjacent reflections are measured and the driver is configured to drive the transducer producing the sound wave based on the measurement of timing difference between adjacent reflections.

Another exemplary embodiment provides a method of controlling the energy of sound waves generated in a fluid sensing system using a predetermined threshold. The method includes generating, with a transducer, a first sound and a second sound wave in a tank having a fluid. The method further includes receiving, with the transducer, a first echo of the first and second sound waves. The method further includes comparing, with a controller, a signal characteristic of the first echo of the first sound wave and second sound wave. The method further includes driving, with a driver, the transducer based on comparing the signal characteristic of the first echo of the first and second sound waves.

Other aspects of the invention will become apparent by consideration of the detailed description and accompanying drawings.

BRIEF DESCRIPTION OF THE DRAWINGS

The accompanying figures, where like reference numerals refer to identical or functionally similar elements throughout the separate views, together with the detailed description below, are incorporated in and from part of the specification, and serve to further illustrate embodiments of concepts that include the claimed invention, and explain various principles and advantages of those embodiments.

Figure 1:
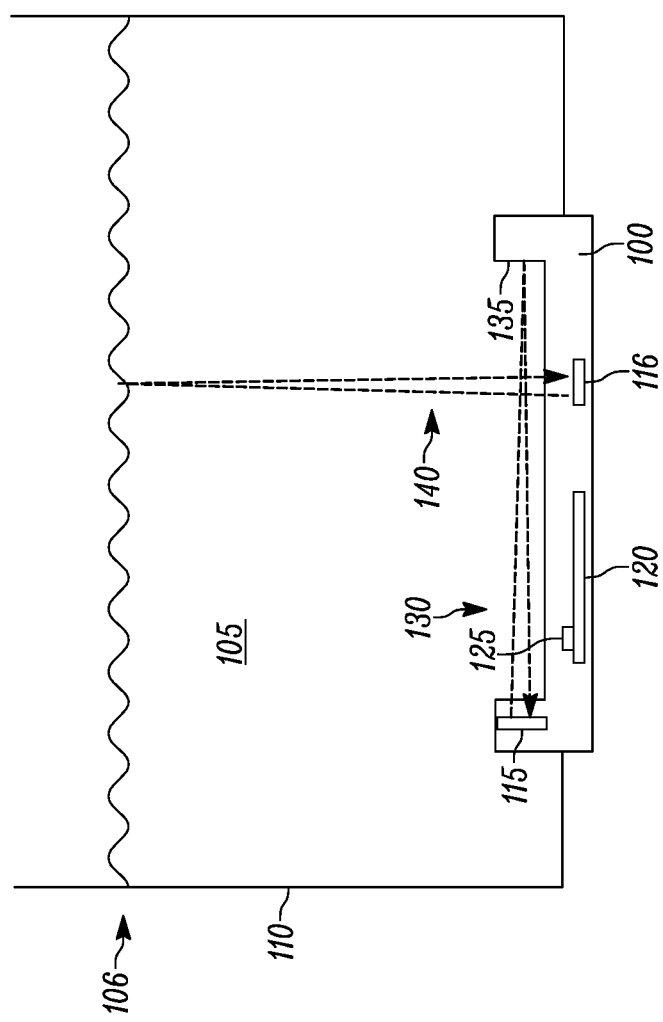
FIG. 1 is a diagram of a fluid sensing system for sensing the quality and the depth of a fluid in a tank, in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

FIG. 1 is a diagram of a fluid sensing system 100 for sensing the quality and the depth of a fluid 105 in a tank 110, in accordance with some embodiments. In the example illustrated, the system 100 includes two piezoelectric ultrasonic transducers 115 and 116 and a temperature sensor 125. In some embodiments, the ultrasonic transducer 115 is a quality transducer (meaning that the signals transmitted and echoes received are used to measure fluid quality) and the ultrasonic transducer 116 is a level transducer (meaning that the signals transmitted and echoes received are used to measure a fluid level). The system 100 also includes a printed circuit board 120 having a temperature sensor 125 (for example, a thermistor) and other components (not shown). The transducer 115 and the printed circuit board 120 are positioned at the bottom of the tank 110. The temperature sensor 125 is positioned such that the temperature sensor 125 detects the temperature of the fluid 105 in the tank 110. The transducers 115 and 116 act as both a transmitter and a receiver. Ultrasonic sound waves 130 generated by the transducer 115 propagate through the fluid 105 and are reflected off of a reflector 135 back towards the transducer 115. The reflected ultrasonic sound wave 130 is detected by transducer 115, and reflects off the transducer 115 back towards the reflector 135. Ultrasonic sound waves 140 generated by the transducer 116 propagate through the fluid 105 and are reflected off of a surface 106 (of the fluid 105) back towards the transducer 116. The ultrasonic sound wave 130 travels back and forth between the reflector 135 and the transducer 115 multiple times. The ultrasonic sound wave 140 travels back and forth between the surface 106 and the transducer 116 multiple times. The system 100 can be integrated into the tank 110 or can be a separate assembly mounted in the tank 110.

Figure 2:
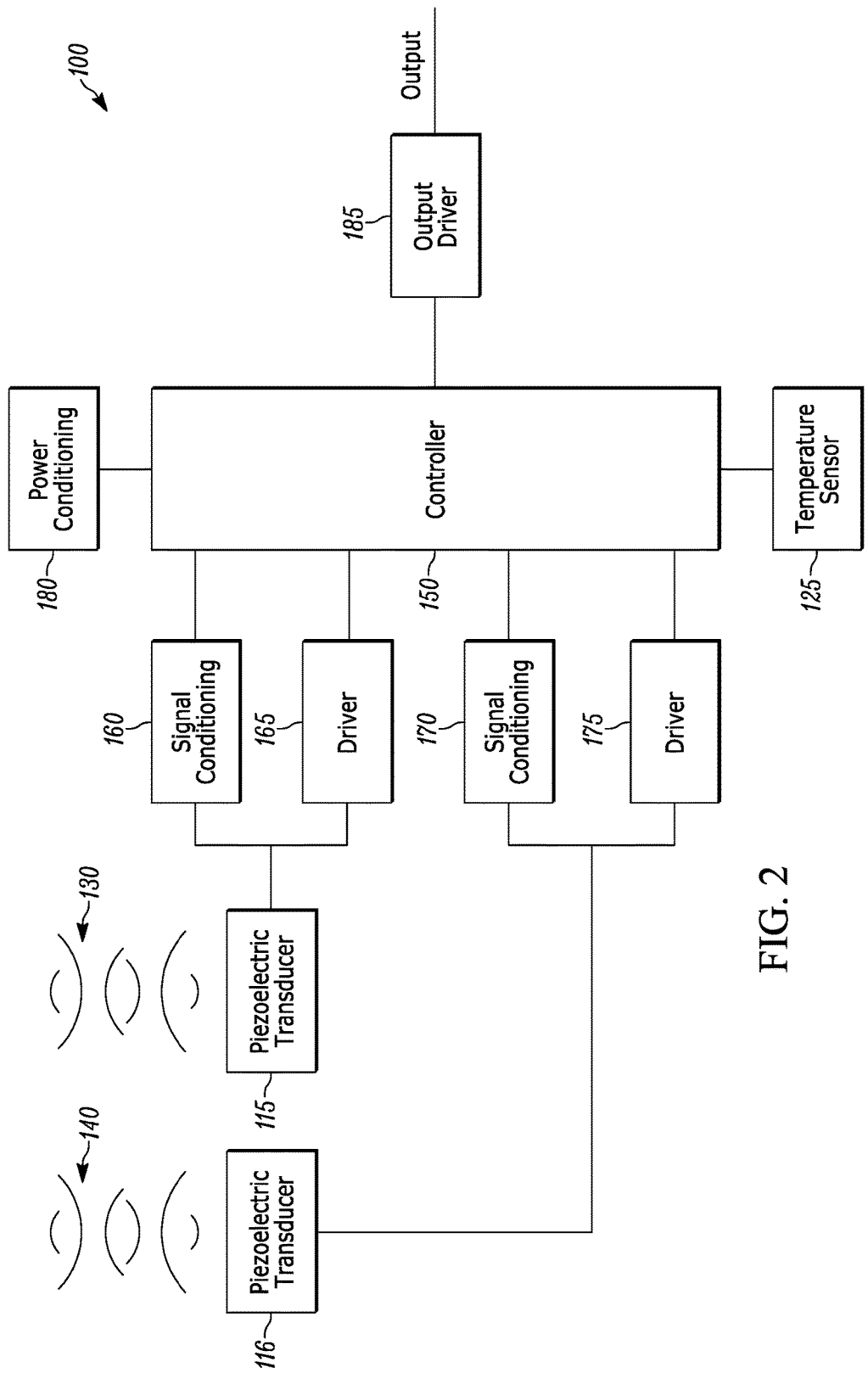
FIG. 2 is a block diagram of the fluid sensing system in FIG. 1, accordance with some embodiments.

FIG. 2 is a block diagram of the fluid sensing system 100 in FIG. 1, in accordance with some embodiments. In the example illustrated, the sensing system 100 includes a quality transducer 115 and a level transducer 116. The fluid sensing system 100 also includes a controller 150, a first signal conditioning circuit 160, a second signal conditioning circuit 170, a first driver 165, a second driver 175, a power conditioning circuit 180, and an output driver 185. The controller 150 includes an electronic processor (for example, a microprocessor, microcontroller, application specific integrated circuit (ASIC), digital signal processing circuit, etc.) and memory (for example, flash, ROM, RAM, EEPROM, etc.) which can be internal to the controller 150, external to the controller 150, or a combination thereof. The electronic processor fetches and executes instructions saved in the memory. The memory can store data used or created by the electronic processor as part of executing instructions. The electronic processor may be implemented using one, two, or another number of processors. In some embodiments, the controller 150 includes one or more signal conditioning circuits 160 and 170, drivers 165 and 175, temperature sensors 125, and output drivers 185. The transducers 115 and 116 operate in two modes, for example, as a piezoelectric transmitter and as a piezoelectric receiver. When the transducers 115 and 116 are stimulated by an electric voltage at a resonant frequency of the piezoelectric crystals of the transducers 115 and 116, the transducers 115 and 116 emit the ultrasonic sound waves 130 and 140, respectively. When the transducers 115 and 116 are stimulated by ultrasonic sound waves 130 and 140, respectively, (for example, an echo) at a resonant frequency of the transducer 115 and 116, the transducers 115 and 116 generate an output signal indicative of the received sound wave. In some embodiments, the first signal conditioning circuit 160 serves to amplify and filter a signal received from the quality transducer 115 in response to being simulated by a received echo from ultrasonic sound wave 130. In some embodiments, the second signal conditioning circuit 170 serves to amplify and filter a low-level signal received from the level transducer 116 in response to being stimulated by a received echo from ultrasonic sound wave 140.

In operation of one exemplary embodiment, the controller 150 is configured to measure specific gravity or concentration of the fluid that relates to the quality in the case of diesel exhaust fluid, and or viscosity/grade in the case of oils. The controller 150 sends a low-level series of drive pulses and a drive pulse amplitude command signal to the drivers 165, 175. The drive pulses are at the constant frequency of the transducer 115/116. The drivers 165, 175 amplifies the low-level signal, applying a series of high voltage pulses to the transducer 115/116, causing the transducer 115/116 to emit the ultrasonic sound wave 130/140 at an amplitude proportional to amplitude and the number of resonant drive pulses applied to the transducer 115/116. The ultrasonic sound wave 130/140 propagates through the fluid and is reflected off of the reflector 135 or the surface 106 back towards the transducer 115/116. The returned ultrasonic transducer echo causes transducer 115/116 to resonate, creating a low-level voltage signal which is amplified, filtered, and shaped by signal conditioning circuit 160 and detected by the controller 150. The time necessary for the ultrasonic sound wave 130/140 to propagate through the fluid 105 from the transducer 115/116 to the reflector 135/surface 106 is stored in the memory of the controller 150 as a first echo reflection. Given sufficient amplitude, the ultrasonic sound wave 130/140 propagates back and forth between transducer 115/116 and the reflector 135/surface 106, creating a series of echo reflections. Typically, 2 or 3 reflections are received and/or detected for a given transmission. The reflections are measured and stored in the memory of the controller 150 for processing.

The number of echo reflections used by the system is dependent on the resolution required to discriminate between contaminant concentration levels in the fluid. For example, if one echo reflection requires a first time to propagate through the fluid from transducer 115/116 reflect off a reflector 135 or surface 106, and return, a second echo reflection will require twice the first time to propagate, and a third echo reflection will require triple the first time, etc. Given this, two reflections provide twice the resolution of one reflection; three reflections provide three times the resolution, and so on. In a typical application, 2 to 3 reflections provide a good balance between the resolution required and the practical dimensions of sensor systems that can readily be assembled into a fluid tank.

The controller 150 generates a command signal which controls and modulates amplitude of the ultrasonic sound wave 130/140 so as to achieve the desired number of echo reflections. The controller 150 performs this function by increasing or decreasing the number and/or amplitude of resonant voltage pulses applied to the temperature-dependent transducer. The number of resonant pulses applied to the transducer typically ranges from a low of 1 pulse to a high of 16 or more pulses, although other numbers of pulses may be applied. A switched capacitor charge pump is preferably used to increase or decrease the amplitude of the transducer drive voltage applied to the driver 165 under the control of controller 150. The drive voltage typically varies from low of 2 volts to a high of 30 volts. The number and amplitude of drive pulses is selected based on the number of echo reflections that are received. If the number of echo reflections falls below a preset quantity (calculated based on the relative distance being discerned), the controller 150 increases the amplitude and/or number of drive pulses. Conversely, if the number of echo reflections is greater than the preset quantity, the controller 150 decreases the amplitude and/or number of drive pulses applied to the transducer 115/116 (reducing unwanted distortion and noise). Thus, a closed loop gain control is created for the transmission and detection of the ultrasonic sound wave 130/140 echo reflections.

In one embodiment, the controller 150 defines a near-field operational mode as that which occurs when the first echo reflection identified occurs during a period of time equal to a slightly greater than twice the average ring time for the transducer 116. The controller 150 defines far-field operational mode as that which occurs when the first echo reflection occurs outside of the time period defined by near-field operational mode or, in one example, if the first echo reflection is received at a time interval greater than that of twice the average ring time for the transducer 116. In near-field mode, the controller 150 modulates the power to the transducer 116 to ensure that at least two validated echo reflections (or another predetermined number) are received following the conclusion of the ring period. In the far-field mode, the controller 150 modulates the power to the transducer 116 to ensure that at least one valid echo reflection is received following the conclusion of the ring period.

The resonant frequency of a piezoelectric crystal, such as transducer 115/116, changes with temperature. The ability to modulate and control the amplitude of the ultrasonic wave 130/140 is dependent on driving the transducer 115/116 at its resonant frequency. In one embodiment, the controller 150 performs this function by changing the frequency of the pulses applied to the transducer 115/116 based on the temperature senses by the temperature sensor 125. The relationship between piezoelectric resonant frequency of the transducer 115/116 and temperature is specific to the selected type, size, shape, and mechanical design of the piezoelectric material. The temperature-dependent relationship is measured empirically for the design, and then it is set forth in the form of a look-up table within the controller 150. Using a frequency specified in the look-up table for the measured temperature, the controller 150 selects and controls the transducer 115/116 drive frequency.

The movement of the fluid, temperature gradients, air bubbles, and contaminants can interfere with the ultrasonic sound waves generated by a transducer, creating shifts in time or generating noise within the received string of echoes. Phase errors and lobe shifts may also create measurement errors in high precision ultrasonic distance measurement applications such as those applied to DEF concentration or oil viscosity measurements.

Figure 3:
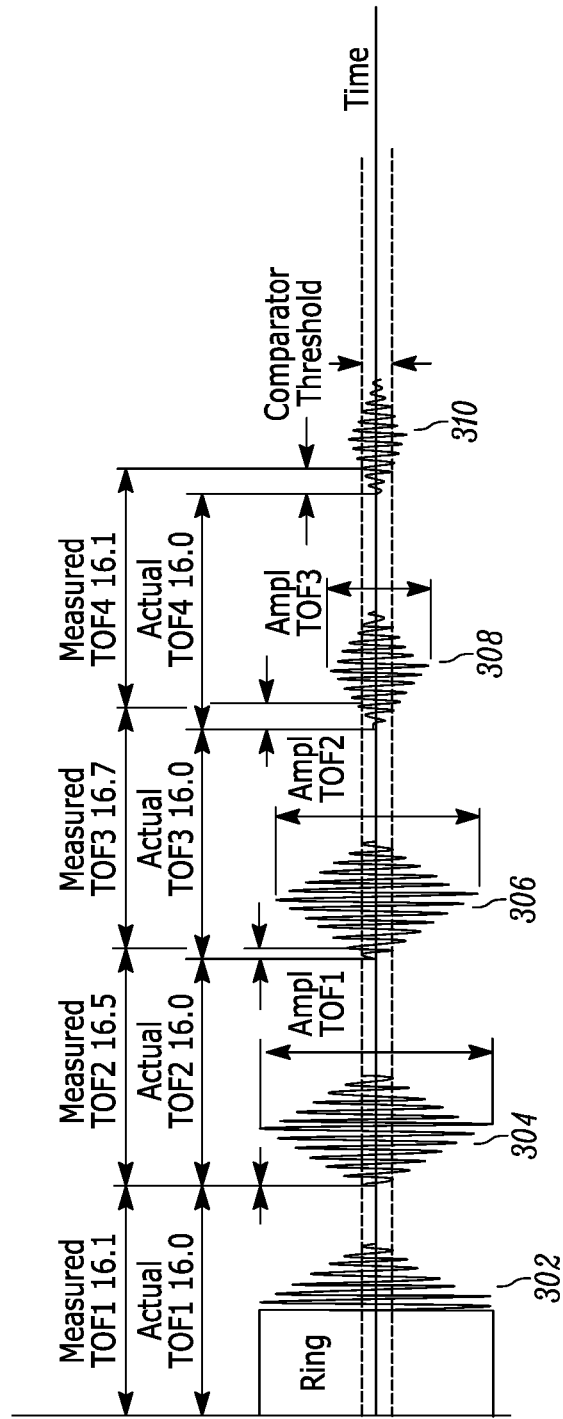
FIG. 3 is a diagram illustrating different sinusoidal return echo generated during ultrasonic distance measurement, in accordance with some embodiments.

FIG. 3 is a diagram illustrating sinusoidal return echoes generated during an ultrasonic measurement, in accordance with some embodiments. FIG. 3 shows an initial ring 302 generated by one of the transducers 115/116 followed by a first echo 304, a second echo 306, a third echo 308, and a fourth echo 310. FIG. 3 also illustrates a first time of flight (TOF1) between the initial ring 302 and the first echo 304, a second time of flight (TOF2) between the second echo 306 and the third echo 308, and a third time of flight (TOF3) between the third echo 308 and the forth echo 310.

A declining excitation power may cause a lobe shift to occur where the amplitude of the first sinusoidal cycle in an echo may fall below a predetermined threshold. At least in certain embodiments, a lobe shift is a measurement error that occurs when the amplitude of the returned pulse falls below the comparator threshold thus causing the measured TOF to increase by 1/f.

For example, the first sinusoidal in the second echo 306 is below a predetermined threshold. Therefore, the time of flight between subsequent echoes, i.e. first echo 304 and second echo 306 will increase by 1/freq(F) as can be seen in FIG. 3. This is further illustrated in FIG. 3, as the measured TOF2 is 16.5 microseconds as opposed to an actual TOF2 of 16 microseconds. In this case, the measured shift of dropping the first sinusoidal lobe is 0.4 microseconds which would create a considerable error if this difference of 0.4 microseconds were to be used for measurement. Also shown in FIG. 3 is a phase error associated with TOF1 of 0.1 microseconds due to a finite slope of the sinusoidal return echo. This error may also be problematic but not to the extent of the above case of dropping an entire lobe. In one embodiment, the above described errors may be avoided by having the controller 150 detect that a lobe shift has occurred and then increase the output power of driver 165/175 accordingly. Power is increased, but not so much to create unwanted echoes or interferences from other far-field objects or temperature thermoclines within the fluid being measured. Using this technique, the phase error problem in the received echo may be reduced, as is described in further detail below.

Figure 4:
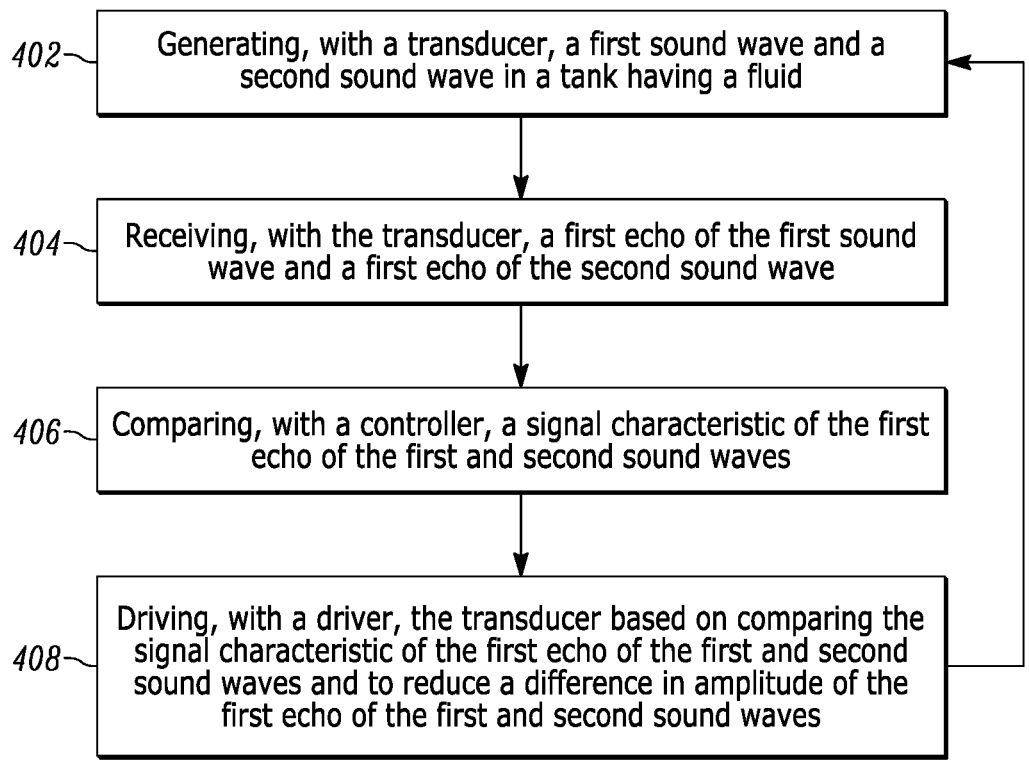
FIG. 4 is a flow chart of the method of controlling the energy of sound waves in a fluid sensing system, in accordance with some embodiments.

FIG. 4 is a flow chart of the method of controlling the energy of sound waves in a fluid sensing system, in accordance with some embodiments. In the example shown, the method begins with the transducer 115 generating a first sound wave and a second sound wave in the tank 110 having a fluid 105 (Step 402). The transducer 115 then receives a first echo of the first sound wave and a first echo of the second sound wave (Step 404). The controller 150 then compares the signal characteristic of the first echo of the first and second sound waves (Step 406). In some embodiments, the signal characteristic of the first echo of the first and second sound waves includes at least one of an amplitude differential, a phase difference, and/or a difference in the timing between adjacent TOF returns due to a lobe shift. The driver 165 then drives the transducer 115 based on comparing the signal characteristic of the first echo of the first and second sound waves and is configured to reduce a difference in amplitude of the first echo of the first and second sound waves. (Step 408). In an example, driving the transducer 115 includes changing the output power of the transducer 115 and generating a sound wave based on comparing the amplitude of the echo of the sound wave to the predetermined threshold. In one embodiment, generating the second sound wave includes producing not more than two echoes of the second sound wave which vary in TOF by a maximum of 1/freq (F). In an alternate embodiment, generating the second sound wave includes determining a maximum power of the first sound wave at which the amplitude of a lobe of the first echo of the first sound wave falls below a threshold. In some embodiments, generating the second sound wave includes producing an echo having a phase error within the predetermined threshold. In some embodiments, the controller 150 is configured to compare the signal characteristic of the first echo of the first and second sound waves by comparing a phase error of the first echo of the first and second sound waves with a predetermined threshold. Some of distance measurement errors that occur due to phase errors and lobe shifts may be addressed by (1) addressing power for specific number of detects, (2) adjusting power based on lobe shifts, (3) adjusting power based on received echo amplitude, and (4) adjusting power based on phase of the received echo. These techniques are discussed in further detail below.

Adjusting Power for a Specific Number of Detects

In some embodiments, the controller 150 is configured to adjust the output power of the driver 165 in such a way to produce two or more echoes. The corresponding time of flight for each echo (for example, TOF1 and TOF2) is recorded. Following which, the output power of the driver 165 is reduced until the third echo is made to disappear and the corresponding time of flight measurements are recorded (for example, TOF$1^1$ and TOF$2^1$). When the measured TOF1 and TOF$1^1$ are within a predetermined limit (typically within one microcontroller timer count) then the measured time of flight is used for further processing. In some embodiments, a differential measurement may be made between TOF1 and TOF2 and compared with the differential measurement between TOF$1^1$ and TOF$2^1$ within a predetermined limit (for example, one microcontroller timer count).

Adjusting Power Based on Lobe Shifts

In some embodiments, the controller 150 is configured to adjust the output power of the driver 165 in such a way to produce two or more echoes. The corresponding time of flight for each echo (for example, TOF1 and TOF2) is recorded. Following which, the output power of the driver 165 is reduced until a lobe within a particular echo falls below a comparator threshold. In an example, the output power is increased until TOF1 and the difference between TOF1 and TOF2 are within 1/freq(F) of each other. This implies that they are more or less in phase within 360 degrees or less. Following which, the controller 150 is configured to reduce the output power of the drivers 165 until the TOF1$^1$ and the difference between TOF1$^1$ and TOF2$^1$ are within 2/freq(F) of each other meaning that one lobe has been shifted, presumably in TOF2. If TOF1 and TOF1$^1$ are more or less equal within the predetermined limit, typically one microcontroller timer count, then the TOF1 measurement is plausible. In some embodiments, a differential measurement between TOF1 and TOF1$^1$ is made and determined to be within a predetermined limit and in which case the differential time would be the time difference between TOF2 and TOF1.

Adjusting Power Based on Received Echo Amplitude

In some embodiments, the controller 150 is configured to detect the peak amplitude of each echo and determine the capture of received echoes based on their peak amplitude. The amplitude of a received echo is determined for an acceptable phase error for TOF1 and/or TOF2 through TOFN and the output power to driver 165 is managed in such way that acceptable phase error limits are achieved. In an example, the controller 150 is configured to use only the TOF measurements having corresponding amplitudes within the predetermined acceptable range.

Adjusting Power Based on the Phase of the Received Echo

In some embodiments, the controller 150 is configured to manage the output power of driver 165 by determining the phase of two adjacent echoes. In an example, the controller 150 determines the phase of a first echo 304 and a second echo 306. In some embodiments, when a relative phase difference between first echo 304 and second echo 304 falls below a predetermined limit then the TOF1 of the first echo 304 and TOF2 of the second echo 306 may be used for fluid level and/or fluid quality measurement.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

It should be noted that a plurality of hardware and software based devices, as well as a plurality of different structural components may be utilized to implement the invention.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (for example, comprising a processor) to perform a method as described and claimed herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method of controlling energy of sound waves generated in a fluid sensing system, the method comprising:
generating, with a transducer, a first sound wave and a second sound wave in a tank having a fluid;
receiving, with the transducer, a first echo of the first sound wave and a first echo of the second sound wave;
comparing, with a controller, a signal characteristic of the first echo of the first and second sound waves; and
driving, with a driver, the transducer based on comparing the signal characteristic of the first echo of the first and second sound waves and to reduce a difference in amplitude of the first echo of the first and the second sound waves.

2. The method of claim 1, further comprising:
comparing, with the controller, the signal characteristic of the first echo of the first and second sound waves to a predetermined threshold.

3. The method of claim 2, wherein comparing the signal characteristic of the first echo of the first and second sound waves includes comparing a phase error of the first echo of the first and second sound waves with the predetermined threshold.

4. The method of claim 1, wherein the signal characteristic is selected from the group consisting of an amplitude, a phase, and a lobe shift.

5. The method of claim 1, wherein driving the transducer includes changing an output power of the transducer and generating a third sound wave based on comparing amplitudes of the first echo of the first and the second sound waves to the predetermined threshold.

6. The method of claim 5, wherein driving the transducer includes changing an output power of the transducer to generate not more than two echoes of the second sound wave.

7. The method of claim 1, wherein generating the second sound wave includes determining a power of the first sound wave at which an amplitude of a lobe of the first echo of the first sound wave falls below a threshold.

8. A fluid sensing system, the system comprising:
a transducer configured to generate a first sound wave and a second sound wave and to detect a first echo of the first and second sound waves;
a driver configured to drive the transducer to produce the first and second sound waves; and
a controller configured to
compare a signal characteristic of the first echo of the first and second sound waves, and
control the driver based on comparing the signal characteristic of the first echo of the first and second sound waves, in order to reduce a difference in amplitude of the first echo of the first and second sound waves.

9. The fluid sensing system of claim 8, wherein the signal characteristic is selected from the group consisting of amplitude, phase and lobe shift.

10. The fluid sensing system of claim 9, wherein the driver is configured to change an output power of the transducer and generate a third sound wave based on the amplitude of the first echo of the first and second sound waves.

11. The fluid sensing system of claim 10, wherein the output power of the transducer is configured to generate not more than two echoes of the first and second sound waves.

12. The fluid sensing system of claim 8, wherein the controller is configured to compare the signal characteristic of the first echo of the first and second sound waves to a predetermined threshold.

13. The fluid sensing system of claim 12, wherein the controller is configured to determine a power of the first sound wave at which the amplitude of a lobe of the first echo is equal to the predetermined threshold.

14. The fluid sensing system of claim 12, wherein a phase error of the first echo of the first and second sound waves is within the predetermined threshold.

15. A system for controlling energy of sound waves generated for fluid sensing, the system comprising:
a controller comprising a memory and an electronic processor executing computer-readable instructions that cause the system to:
generate a first sound wave and a second sound wave in a tank having a fluid;
receive a first echo of the first sound wave and a first echo of the second sound wave;
compare a signal characteristic of the first echo of the first and second sound waves;
drive a transducer based on comparing the signal characteristic of the first echo of the first and second sound waves; and
reduce a difference in amplitude of the first echo of the first and the second sound waves.

* * * * *